United States Patent [19]

Torossian et al.

[11] 4,301,163
[45] Nov. 17, 1981

[54] AMINO-ETHER OXIDES AND USE THEREOF IN THERAPY

[75] Inventors: Diéran R. Torossian, Bourg-la-Reine; Claude P. Roux, Paris; Gilbert G. Aubard, Palaiseau, all of France

[73] Assignee: Societe Industrielle de Produits de Synthese, Avrille, France

[21] Appl. No.: 164,931

[22] Filed: Jul. 1, 1980

[30] Foreign Application Priority Data

Jul. 11, 1979 [FR] France ................. 79 17986

[51] Int. Cl.³ ............ A61K 31/44; A61K 31/13; C07C 87/28; C07D 213/36
[52] U.S. Cl. ................. 424/263; 424/330; 546/300; 546/334; 564/346; 564/347
[58] Field of Search ............ 564/346, 347; 424/330, 424/263; 546/292, 300, 334

[56] References Cited

U.S. PATENT DOCUMENTS 3,106,564 10/1963 Fleming et al. .............. 564/347
4,194,009 3/1980 Molloy et al. ............... 564/347
4,207,343 6/1980 Lavagnino et al. ........... 564/346

Primary Examiner—Natalie Trousof
Assistant Examiner—Leah Hendriksen
Attorney, Agent, or Firm—Cushman, Darby & Cushman

[57] ABSTRACT

Amino-ether oxides of formula:

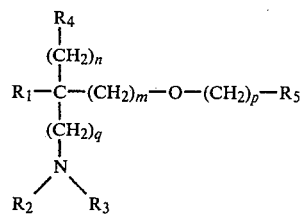

in which $R_1$ is lower alkyl, $R_2$ and $R_3$ which are the same or different are hydrogen or lower alkyl, $R_4$ is a phenyl or phenoxy nucleus optionally monosubstituted to trisubstituted by substituents which are the same or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, n is equal to zero, 1 or 2 and p is an integer from 0 to 9, m and q are equal to zero or 1.

Local and spasmolytic anaesthetics.

9 Claims, No Drawings

AMINO-ETHER OXIDES AND USE THEREOF IN THERAPY

The present invention relates to novel amino-ether oxides, a process for the preparation thereof and use thereof in human and veterinary medicine.

The amino-ether oxides according to the invention conform to the formula:

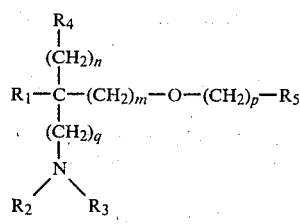

in which:
$R_1$ is a lower alkyl, $R_2$ and $R_3$ which are the same or different are hydrogen or lower alkyl, $R_4$ is a phenyl or phenoxy nucleus optionally monosubstituted to trisubstituted by substituents which are identical or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, n is equal to zero, 1 or 2, m and q are, independently of one another, equal to zero or to 1, p is an integer ranging from 0 to 9.

By lower radical are meant radicals having from 1 to 10 carbon atoms, preferably 1 to 6 carbon atoms, especially 1 to 4 carbon atoms in a straight or branched chain.

If $R_5$ is alkyl, it is preferably methyl. If the amino-ether oxides are halogenated, they are preferably brominated or chlorinated.

The invention also embraces the acid addition salts of amino-ether oxides, notably those of mineral acids, such as halohydrates, sulphates, phosphates, or organic acids such as maleates, citrates, malates, tartrates, methanesulphonates, camphosulphonates, benzoates, etc.

The invention covers both racemic and optionally active forms which can be separated, particularly by forming salts with optically active acids.

To prepare the amino-ether oxides according to the invention, a compound of formula AX can be condensed with an alcoholate of formula BOM, one of A and B being the radical

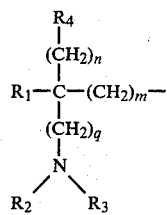

when the other is the radical $R_5$—$(CH_2)_p$—, X being an anionic radical and M being an alkali metal, the acid addition salts being obtained conventionally by salification by means of the selected acid.

X preferably represents bromine or chlorine, but it can also be an anionic sulphate, benzosulphonate, methanesulphonate or p-toluenesulphonate radical.

The alcoholates in which the radicals $R_1$ to $R_4$ appear can be prepared by reacting an alkali metal M, especially sodium or potassium or their hydrides or amides, with the corresponding amino-alcohols prepared as described in French Pat. Nos. 912,577 or 71.08700 or according to the method described by Chapman and Triggle in "J. Chem. Soc." 1963, page 4835. The reaction is effected in aromatic solvents such as benzene, toluene, xylenes or in ether solvents such as diethyl ether, dioxane, tetrahydrofuran or aprotic solvents such as dimethyl sulphoxide, dimethyl formamide (DMF), acetonitrile, dimethyl acetamide, hexamethyl phosphorotriamide (HMPT); this last group of solvents is especially preferred when the salification agent is in the form of the hydride or amide of the alkali metal M.

The reaction is effected at a temperature of between 0° and 140° C., especially between 20° and 110° C.

The reaction time varies according to the reagents and the temperature and is between 15 minutes and 24 hours, especially between 30 minutes and 6 hours.

The reactive esters and particularly the halides in which the radical $R_5$ appears are prepared according to the method of Shepard and Noth described in the "Journal of the American Chemical Society" 1950, page 4364, in which alcohol is reacted with thionyl chloride, or according to the method of Ctvrtnik described in "Chemical Abstracts" 1956, Vol. 50 10130 c, by chloromethylation of aromatic nuclei. The halides and others in which the radicals $R_1$ to $R_4$ appear are prepared, for example, according to the method described in "Organic Syntheses" Coll. Vol. IV, page 333, or by the numerous other methods referred to in this article.

These latter methods generally make it possible to obtain a product which can be used in the following condensation reaction:

either as such by releasing in situ the reactive ester from its salt by the action of a strong base such as an amine, for example triethylamine, or any other product which can effect this displacement;

or by displacing in a previous stage the amino-alcohol ester from its salt by the action of a suitable alkaline agent such as sodium hydroxide, extraction of the liberated product by means of an organic solvent such as, for example, diethyl ether or chloroform, then evaporation of this extraction solvent which leads to the reactive amino-alcohol ester which is used as such or in solution in the solvent suitable for the following condensation reaction.

The condensation of AX and of BOM is effected at a temperature of between 0° and 140° C., preferably between 70° and 110° C. The reaction time is between 1 and 24 hours, preferably between 4 and 12 hours. The progress of the reaction can be followed by thin-layer chromatography.

The amino-ether oxide is separated from the reaction medium by methods well known to a person skilled in the art, such as, for example, extraction, precipitation, fractional distillation, crystallisation of salts, etc.

The following Examples illustrate the invention.

EXAMPLE 1 (preferred)

1-[(3,4-dimethoxy)benzyloxymethyl]-1-phenyl-N,N-dimethyl-n-propylamine $R_1$=ethyl, $R_2$=$R_3$=methyl, $R_4$=phenyl, $R_5$=,4-dimethoxyphenyl, n=q=0, m=p=1.

39.3 grams of sodium (1.71 mol) are introduced into 300 grams of 2-phenyl-2-dimethylamino-1-butanol (1.55 mol) in solution in 3 liters of anhydrous dioxane.

The mixture is refluxed with vigorous stirring to disperse the sodium.

After 6 hours 434 grams of 3,4-dimethoxy-α-chlorotoluene (2.34 mol) in solution in 1 liter of anhydrous dioxane are introduced within 30 minutes; the mixture is maintained for 6 hours at the reflux temperature of the solvent.

The suspension is filtered and the solvent of the filtrate is eliminated by distillation in vacuo.

The residue is taken up with 2 liters of hydrochloric acid (2N) and extracted with diethyl ether. The ether phases are removed and the aqueous acid phase is made alkaline in the cold with sodium hydroxide solution (10N) in a quantity sufficient to obtain a pH value of 12.

The oil formed is extracted with ether, the ether phases are washed with water and then dried over sodium sulphate and the ether is eliminated by distillation.

The oily residue obtained is purified by fractionation in vacuo.

$B.p._{0.2/0.5}$=187°–193° C., weight: 271 grams, yield≃50%.

The DL camphosulphonate of the product is prepared in ethanol and recrystallised in ethyl acetate.

Yield=85%, M.p.=108° C.

EXAMPLE 2 (preferred)

1-[(3,4,5-trimethoxy)benzyloxymethyl]-1-phenyl-N,N-dimethyl-n-propylamine $R_1$=ethyl, $R_2$=$R_3$=methyl, $R_4$=phenyl, $R_5$=3,4,5-trimethoxyphenyl, n=q=0, m=p=1.

2.07 kg of oily suspension of sodium hydride at 60% (51.75 mol) in 11.6 liters of anhydrous dimethylformamide (DMF) are introduced into a suitable reactor.

With stirring and maintaining the reaction temperature below 40° C. about 10.00 kg of 2-phenyl-2-dimethylamino-1-butanol (51.70 mol) in solution in 8.7 liters of anhydrous DMF are introduced within 45 minutes.

After introduction the suspension is maintained for 45 minutes at about 40° C. 11.20 kg (51.70 mol) of 3,4,5-trimethoxy-α-chlorotoluene in solution in 8.7 liters of anhydrous DMF are subsequently introduced within about 35 minutes and without exceeding 60° C.

The mixture is subsequently maintained for 5 hours at 70° to 75° C. and is then cooled to 20° c.

The suspension obtained is introduced into 250 liters of iced water and is then acidified with concentrated hydrochloric acid until a pH value of 1 is obtained.

The mixture is extracted with toluene. The toluene phases are removed and the aqueous acid phase is made alkaline until a pH value of 12 is obtained with a sodium hydroxide solution (10N) and the mixture is extracted with methylene chloride. The methylene chloride phases are washed with water, dried over $Na_2SO_4$ and the methylene chloride is eliminated by distillation.

The residue is solubilised in 200 liters of hexane at boiling point, filtered hot and the filtrate cooled with stirring.

After the start of crystallisation the suspension is left overnight at 10° C.

The product is filtered, washed with cold hexane and dried in vacuo at ambient temperature.

Weight=12.2 kg, yield=63%, M.p.=55°–56° c.

The hemi-maleate of the product is prepared and recrystallised in water.

Yield=90%, M.p.=123°–124° C.

EXAMPLE 3 (preferred)

1-Benzyloxymethyl-1-phenyl-N,N-dimethyl-n-propylamine $R_1$=ethyl, $R_2$=$R_3$=methyl, $R_4$=$R_5$=phenyl, n=q=0, m=p=1.

4.0 grams of sodium hydride at 90% (0.15 mol) are introduced into 30.0 ml of hexamethyl phosphorotriamide (HMPT).

A solution of 29.0 grams (0.15 mol) of 2-phenyl-2-dimethylamino-1-butanol in 30 ml of HMPT is introduced with stirring over about 30 minutes and without exceeding 30° C.

Stirring is maintained for 30 minutes after introduction and 19.0 grams of α-chlorotoluene (0.15 mol) in solution in 30 ml of HMPT are then added over 30 minutes at a temperature below 40° C.

The suspension is then maintained with stirring for 5 hours at 70° to 75° C. and is then left overnight at ambient temperature.

The reaction medium is precipitated in 1 liter of iced water and the mixture is acidified with hydrochloric acid in a quantity sufficient to obtain a pH value of 1 and is extracted with diethyl ether. The ether phases are eliminated and the aqueous acid phase is made alkaline by a sodium hydroxide solution until a pH value of 12 is obtained.

The suspension is extracted with diethyl ether, the combined ether phases are washed with water and dried over anhydrous sodium sulphate and the ether is then eliminated by distillation.

The residue is purified by fractional distillation in vacuo.

$B.p._{0.25}$=157°–158° C., weight=21 grams, yield=49.4%.

The maleate of the product is prepared in ethanol and recrystallised in water.

Yield=95%, m.p.=113°–114° C.

According to the process described in Example 3, the amino-ether oxides listed in table 1 below are obtained from 2-phenyl-2-dimethylamino-1-butanol and halides of formula $R_5$—$(CH_2)_p$X.

TABLE 1

| Example No | p | X | $R_5$ | YIELD | Characteristics |
|---|---|---|---|---|---|
| 4 | 3 | Br | —$CH_3$ | 30% | $Bp_{1.2}$ = 118–119° C. |
| 5 | 9 | Br | —$CH_3$ | 18% | $Bp_{0.1}$ = 170–175° C. |
| 6 | 1 | Cl | —⟨◯⟩—$CH_3$ | 72% | $Bp_{0.6}$ = 161–172° C. |
| 7 | 0 | Cl | ⟨◯⟩–N | 46% | $Bp_{0.6}$ = 135–140° C. |
| 8 | 0 | Cl | ⟨◯⟩–N | 53% | $Bp_{0.5}$ = 150–152° C. |

TABLE 1-continued

| Example No | p | X | R5 | YIELD | Characteristics |
|---|---|---|---|---|---|
| 9 | 1 | Cl | 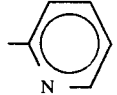 | 66% | Bp$_{0.6}$ = 135–145° C. |
| 10 | 1 | Cl | 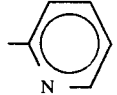 | 52% | Bp$_{0.8}$ = 162–163° C. |

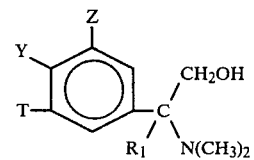

and from halides R$_5$—(CH$_2$)$_p$—X.

TABLE 2

Structures

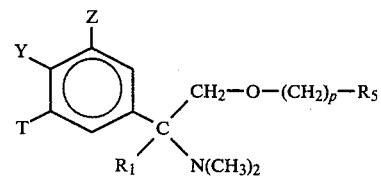

| Example No | R$_1$ | p | X | R$_5$ | Z | Y | T | Yield | Characteristics |
|---|---|---|---|---|---|---|---|---|---|
| 13 Preferred compound | CH$_3$ | 1 | Cl | —Cl | H | OCH$_3$ | H | 35% | Maleate Mp = 102–105° C. |
| 14 | CH$_3$ | 1 | Cl |  | OCH$_3$ | OCH$_3$ | OCH$_3$ | 80% | DL camphosulphonate Mp = 80° C. |
| 15 | CH$_3$ | 1 | Cl | —CH$_3$ | Cl | Cl | H | 70% | DL camphosulphonate Mp = 154° C. |
| 16 | C$_2$H$_5$ | 1 | Cl | —Cl | OCH$_3$ | OCH$_3$ | H | 33% | DL camphosulphonate Mp = 120° C. |

EXAMPLE 11

2-[(3,4,5-trimethoxy)benzyloxy]-2-phenyl-N,N-dimethyl-n-butylamine

R$_1$=ethyl, R$_2$=R$_3$=methyl, R$_4$=phenyl, R$_5$=3,4,5-trimethoxyphenyl, n=m=0, p=q=1.

Prepared according to the process described in Example 3 from 1-phenyl-1-dimethylaminomethyl-1-propanol and from 3,4,5-trimethoxy-α-chlorotoluene.

Yield=70.5%, m.p.=84°–85° C.
Hydrochloride m.p.=208°–209° C.

EXAMPLE 12 (preferred)

1-[(3,4,5-trimethoxy)benzyloxymethyl]-1-phenyl-N-methyl-n-propylamine

R$_1$=ethyl, R$_2$=H, R$_3$=methyl, R$_4$=phenyl, R$_5$=trimethoxyphenyl, n=q=0, m=p=1.

Prepared by the process of Example 3 from 2-phenyl-2-methylamino-1-butanol and from 3,4,5-trimethoxy-α-chlorotoluene; the product is obtained in the form of a colourless and viscous oil which is analytically pure and appropriate.

Yield=60%, n$_D^{20}$=1.5491.

The corresponding amino-ether oxides and/or their salts listed in table 2 are obtained according to the process described in Example 3 and from amino-alcohols of structure

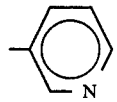

EXAMPLE 17

1-Benzyloxymethyl-1-methyl-(3,4-dimethoxy)-phenethyl-amine

R$_1$=methyl, R$_2$=R$_3$=H, R$_4$=3,4-dimethoxyphenyl, R$_5$=phenyl, m=n=p=1, q=0.

Using the process described in Example 3 and starting from 2-[(3,4-dimethoxy)benzyl]-2-amino-1-propanol and from benzyl chloride the product is obtained which is crystallised in hexane.

Yield=47%, m.p. 97°–101° C.

According to the process described in Example 3 with amino-alcohols of structure

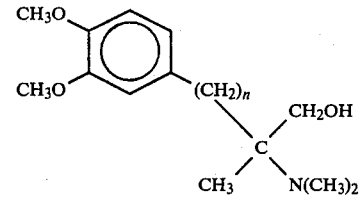

R$_1$=R$_2$=R$_3$=methyl, R$_4$=3,4-dimethoxyphenyl, q=0, m=1, and the halides R$_5$—(CH$_2$)$_p$—X, the following amino-ether oxides are obtained.

| Example No | n | X | p | R$_5$ | Yield | Characteristics |
|---|---|---|---|---|---|---|
| 18 | 1 | Cl | 1 |  | 62% | Maleate Mp = 155–157° C. |

-continued

| Example No | n | X | p | R5 | Yield | Characteristics |
|---|---|---|---|---|---|---|
| 19 | 2 | Cl | 1 | (2,4,5-trimethoxyphenyl: OCH3, OCH3, OCH3) | 47% | Base $n_D^{20} = 1.5405$ |

EXAMPLE 20

1-[(2-methoxy-5-nitro)benzyloxymethyl]-1-[(4-chloro)-phenoxymethyl]-N,N-dimethylethylamine $R_1 = R_2 = R_3 = $ methyl, $R_4 = $ (4-chloro)phenoxy, $R_5 = $ 2-methoxy-5-nitrophenyl, $n = m = p = 1$, $q = 0$.

Prepared according to the process of Example 3, starting from 3-[(4-chloro)phenoxy]-2-dimethylamino-2-methyl-1-propanol and from 2-methoxy-5-nitro-α-chlorotoluene.

Yield = 10%, $n_D^{20} = 1.5585$.

EXAMPLES 21 AND 22

21:

1-[(4-methoxy)phenoxymethyl]-1-phenyl-N,N-dimethyl-n-propylamine.

$R_1 = $ ethyl, $R_2 = R_3 = $ methyl, $R_4 = $ phenyl, $R_5 = $ 4-methoxyphenyl, $n = p = q = 0$, $m = 1$.

22:

2-[(4-methoxy)phenoxy]-2-phenyl-N,N-dimethyl-n-butylamine.

$R_1 = $ ethyl, $R_2 = R_3 = $ methyl, $R_4 = $ phenyl, $R_5 = $ 4-methoxyphenyl, $m = n = p = 0$, $q = 1$.

100.0 grams of 4-methoxyphenol (0.80 mol) are dissolved in 1 liter of methanol. 250 ml of a methanolic solution of sodium methylate (0.80 mol) are then added with stirring and stirring is continued for 1 hour 30 minutes, the methanol then being eliminated by distillation in vacuo on a water bath at 60° C.; 117 grams of a beige yellow product are obtained which are used directly in the condensation reaction.

100 grams (0.40 mol) of 2-phenyl-2-dimethylamino-1-chlorobutane hydrochloride (m.p. = 145°–147° C.) are dissolved in 500 ml of iced water. 500 ml of diethyl ether are added and the mixture is made alkaline when cold by a concentrated sodium hydroxide solution until a pH value of 12 is obtained.

The ether phase is separated and the aqueous phase is re-extracted twice with ether. The combined ether phases are washed with water and then dried over $Na_2SO_4$. The ether is eliminated at 20° C. by distillation in vacuo.

A slightly viscous, colourless to light-yellow liquid is obtained.

Weight = 82.2 grams, yield = 96%.

In a suitable reactor 39.4 grams (0.27 mol) of sodium 4-methoxy-phenolate are dissolved in 125 ml of hexamethylphosphorotriamide (HMPT).

57 grams (0.27 mol) of 2-phenyl-2-dimethylamino-chlorobutane in solution in 57 ml of HMPT are added with stirring over 30 minutes and at ambient temperature.

The reaction mixture is subsequently heated for 4 hours to 70° C. and left to stand overnight.

After precipitation in water and the conventional treatments 52.6 grams of a mixture of the two products are obtained.

By crystallisation of the residue in hexane the 2-[(4-methoxy)phenoxy]-2-phenyl-N,N-dimethyl-n-butylamine (22) is isolated.

Weight = 10.5 grams, yield = 13%, m.p. = 55°–57° C.
Hydrochloride: m.p. = 163°–164° C.

From the mother liquors of this first product 1-[(4-methoxy)phenoxymethyl]-1-phenyl-N,N-dimethyl-n-propylamine (21) is isolated in the form of DL camphosulphonate. Weight = 40.2 grams, yield = 28%, m.p. = 154°–155° C.

As the following toxicological and pharmacological tests demonstrate, the amino-ether oxides according to the invention possess local and spasmolytic anesthetic properties. Certain products also have a considerable analgesic activity. These various properties make the products according to the invention valuable pharmaceutical agents.

The *acute toxicity* of the products of the invention was determined on groups of 20 Swiss OF1 mice weighing 22 to 24 grams by intravenous route. These toxicities are expressed as the $LD_{50}$ corresponding to the dose at which a 50% mortality of the treated animals is noted after 8 days of observation. The limits of confidence of these values were determined by the method of Litchfield and Wilcoxon (J. Pharmacol. Exp. Ther. 1949, pages 96 to 99) and are given in table III.

The *local anaesthetic activity on contact* is determined on the cornea of the rabbit according to a method derived from the technique of Regnier (Regnier J. R. Salle P. Bull. Soc. Pharmacol. 1926 33, 91).

Male albino rabbits weighing 2 to 3 kg are used in groups of 5. The product solution to be tested is injected in a volume of 0.2 ml into the conjunctival sac. The cornea is then stimulated by means of a hair 3, 6, 10, 15, 20, 25, 45 and 60 minutes after injection.

The average number of stimulations is calculated for each group and this number is compared with that obtained with a lidocaine hydrochloride solution of equal concentration. The local anaesthetic activity is thus expressed in relation to this reference product.

The activity of the products is thus compared with that of a known anaesthetic: lidocaine (table IV).

Isolated organs

The spasmolytic activity of the products was studied in vitro with regard to two distinct agonists, namely:

1. barium chloride whose contracting effects was demonstrated on the rat duodenum;
2. nicotine whose contracting effect was demonstrated on the guinea-pig ileum.

The organ fragments were kept alive in a tank containing a solution of Tyrode (37° C., pH 7.2, oxygenated by the mixture $O_2/CO_2$, 95%/5%).

The isotonic contractions were recorded graphically on a physiograph by means of a transducer. For each substance the effect-dose straight line is determined according to semi-logarithmic coordinates and the $EC_{50}$ is calculated graphically, that is the concentration of the substance necessary to reduce by 50% the amplitude of the contraction of convulsant agent. The values obtained are compared with those of spasmolytic agents selected as reference and are determined under the same experimental conditions, namely:

papaverine hydrochloride for the convulsant effect of barium chloride;

hexamethonium dibromide for the convulsant effect of nicotine (table V).

*The analgesic activity* of the products was studied on male Sprague-Dawley rats in groups of 15 by a method derived from that of Randall and Selito (Arch. Int. Pharmacodyn. 1957 (III) page 409). This method consists in causing a painful inflammation in the paw of the rat by injecting 0.1 ml of a 20% brewer's yeast solution, then applying a pressure to the inflammation and determining the value of the pressure at which a painful reaction of the animal appears.

The activity of the products was studied after 1 hour of administration by oral route at the rate of one dose of 100 mg/kg in comparison with untreated animals. In this test aspirin was chosen as reference substance.

The analgesic effect of the products is expressed by the percentage increase of the pressure endured by the treated animals in relation to that endured by the untreated animals.

The results of the analgesic activity of the product tested are expressed in relation to the activity of aspirin administered by oral route at a dose of 100 mg/kg. The results obtained are collated in table VI.

The compounds of the invention show anti-spasmodic, anaesthetic and analgesic activities useful in therapy.

These compounds are useful for all the spasmodic states of the smooth musculature and for the painful syndromes which are associated therewith.

By way of non-limiting example they can be used in:

*gastroenterology,* in oesophagitis, gastroduodenal ulcer, gastritis, biliary dyskinesia, hepatic colic, spasmodic colitis, gastrointestinal malfunction as well as for the treatment of nausea and vomiting;

*urology,* in nephritic colics and pain of the urinary passages;

*gynaecology,* in spasmodic dysmenorrhea and dynamic dystocia (spasms of the cervix);

in *vascular disturbances,* to alleviate the cerebral and peripheral ischemia associated with arterial spasms.

In these indications the unit therapeutic dose of the products is between 10 and 200 mg, preferably between 20 and 100 mg of active ingredient for 100 to 2000 mg of excipient.

The daily therapeutic dose is between 10 mg and 2 grams, preferably between 50 and 500 mg.

The active ingredients of the present invention are administered by the various routes applicable to humans and in the therapeutic forms compatible with these routes.

These various forms prepared from active substances (bases or salts) are produced by methods known per se.

Mention may be made as examples of these preparations of tablets, coated pills, capsules, ovules, powders, solutions, suspensions, ointments, gels and suppositories. The "sustained release" forms of these preparations can likewise be used.

To illustrate in a non-limiting way the production of these preparations, the production of tablets and of injectable isotonic solutions containing the active ingredients of the invention are given below.

| (1) Tablets | mg |
|---|---|
| Active substance according to Example 2 | 50.0 |
| Lactose | 26.5 |
| Mannitol | 55.0 |
| Medicinal white sugar | 11.0 |
| Polyethylene glycol 6000 | 5.0 |
| Magnesium stearate | 2.0 |
| Gelatine | 0.5 |
| Corn starch | 50.0 |
| Total | 200.0 |

The gelatine and medicinal white sugar are dissolved separately in water. The two solutions are mixed and the polyethylene glycol 6000 is added thereto.

The lactose and mannitol are mixed intimately and then the active substance of Example 2, corn starch and the solution obtained above are added in order.

The paste is dried, granulated and screened, while adding the magnesium stearate and corn starch.

The obtained product is homogenised and compressed at the rate of 200.0 mg per tablet.

| (2) Injectable isotonic solution | mg |
|---|---|
| Active substance according to Example 3 | 10 |
| Sodium chloride | 9 |
| Distilled water (sufficient to make) | 1 ml |

The isotonic solution is distributed in ampoules of suitable volume which, after sealing, are sterilised by thermal means known per se or the solution is sterilised by filtration and distributed in ampoules which are then sealed. All these operations are effected under sterile atmosphere.

In the latter case, it is preferable to add to the formula described 1% of benzyl alcohol as bacteriostatic agent, that is 10 mg of this alcohol per ml of solution.

TABLE III $LD_{50}$ of the products of the invention in mice by intravenous route

| Example No. | Salt | LD $_{50}$mg/kg$^{-1}$ | Limits of confidence mg/kg$^-$ |
|---|---|---|---|
| 1 | DL camphosulph | 30 | 29–32 |
| 2 | H. maleate | 42 | 41–43 |
| 3 | H. maleate | 41.4 | 38.5–44.5 |
| 4 | H. maleate | 26.8 | 25.1–28.6 |
| 5 | hydrochloride | 37 | 28–49 |
| 6 | H. maleate | 48.6 | 44.6–55.3 |
| 7 | hydrocholride | 37 | 36–39 |
| 8 | hydrochloride | 52.3 | 48.2–55.8 |
| 9 | hydrochloride | 39 | 37–41 |
| 10 | hydrochloride | 43 | 41–45 |
| 11 | hydrochloride | 46.7 | 42.2–51.6 |
| 12 | hydrochloride | 34 | 30–39 |
| 13 | H. maleate | 48.4 | 45.0–52.2 |
| 15 | DL camphosulph | 160.0 | 143.8–178.0 |
| 17 | hydrochloride | 51.6 | 45.8–58.4 |
| 18 | H. maleate | 27.3 | 25.2–29.6 |
| 19 | hydrochloride | 30.7 | 25–37 |
| 21 | DL camphosulph | 140.4 | 131.4–150.0 |
| 22 | hydrochloride | 59.6 | 55.5–64.0 |
| lidocaine | hydrochloride | 31.5 | |

The $LD_{50}$ of papaverine hydrochloride and of hexamethonium bromide are respectively 33.1 and 21.0 mg/kg.

TABLE IV

Results of the local anaesthetic activity of the products of the invention (activity in 1% solution compared with that of lidocaine hydrochloride at an identical concentration)

| Example No. | Salt | Effect compared with lidocaine |
|---|---|---|
| 1 | DL camphosulph | 1.6 |
| 2 | H. maleate | 2.2 |
| 3 | H. maleate | 1.4 |
| 7 | hydrochloride | 1.1 |
| 9 | hydrochloride | 0.7 |
| 11 | hydrochloride | 1.0 |
| 13 | H. maleate | 1.1 |
| 19 | hydrochloride | 0.95 |
| 12 | hydrochloride | 1.7 |
| 21 | DL camphosulph | 0.45 |

The other compounds of the invention show a comparable local activity.

TABLE V

Spasmolytic activity of the products of the invention compared with
(a) papaverine hydrochloride in the test with $BaCl_2$
(b) hexamethonium dibromide in the nicotine test.

| Example No. | Salt | Rat duodenum Ba Cl$_2$ 50 mg/l | Guinea-pig ileum nicotine 1 mg/l |
|---|---|---|---|
| 1 | DL camphosulph | 2.7 | 0.9 |
| 2 | H.maleate | 5.4 | 1.2 |
| 3 | H.maleate | 0.9 | 3.4 |
| 5 | hydrochloride | 0.5 | 2.2 |
| 7 | " | 1.7 | 1.0 |
| 9 | " | 0.4 | 1.4 |
| 10 | " | 0.4 | 1.7 |
| 11 | " | 1.9 | 2.6 |
| 12 | " | 1.2 | 2.3 |
| 21 | DL. camphosulph | 1.7 | 1.7 |
| papaverine | hydrochloride | 1 | — |
| hexamethonium | dibromide | — | 1 |

The other compounds according to the invention have comparable spasmolytic properties.

TABLE VI

Results of the analgesic activity of the products of the invention at a dose of 100 mg/kg by oral route in relation to aspirin

| Example No. | Salt | Activities |
|---|---|---|
| 1 | DL. camphosulph | 1 |
| 5 | hydrochloride | 2.5 |
| 10 | hydrochloride | 1.8 |
| 11 | hydrochloride | 2.3 |
| aspirin | | 1 |

Index of Activity of the Products of the Invention

An index of activity relating to the products of the invention in relation to the reference substance used in each test was calculated for the local anaesthesia test and the spasmolysis tests in vitro.

This index I was calculated with regard to both the activity and the relative toxicity of the products of the invention in relation to the reference substances, namely lidocain hydrochloride, papaverine hydrochloride and hexamethonium dibromide. To eliminate the differences due to the molecular weights of the products, the calculations were made in mmoles.

$$I = \frac{\frac{EC_{50} \text{mmoles of the product studied}}{EC_{50} \text{mmoles of the reference product}}}{\frac{LD_{50} \text{mmoles of the product studied}}{LD_{50} \text{mmoles of the reference product}}}$$

For the products of the invention the results are collated in the following table VII.

TABLE VII

Relative indices of activity of the products of the invention in relation to:
- lidocaine hydrochloride for local anaesthetic activity;
- papaverine hydrochloride for spasmolytic activity in vitro on the rat duodenum;
- hexamethonium dibromide for spasmolytic activity in vitro on the guinea-pig ileum.

| Example No. | local anaethesia/ lidocaine hydrochloride index | spasmolytic index/papaverine hydrochloride | spasmolytic index/hexamethonium dibromide |
|---|---|---|---|
| 1 | 1.52 | 2.45 | 1.29 |
| 2 | 2.95 | 6.90 | 2.42 |
| 3 | 1.85 | 1.125 | 6.69 |
| 5 | — | 0.56 | 3.85 |
| 7 | 1.30 | 1.89 | 1.75 |
| 9 | 0.875 | 0.475 | 2.62 |
| 10 | — | 0.525 | 3.50 |
| 11 | 1.49 | 2.69 | 5.76 |
| 12 | 1.84 | 1.24 | 4.09 |
| 13 | 1.71 | — | — |
| 19 | 0.92 | — | — |
| 21 | 2.00 | 7.28 | 11.33 |

It is noted that the relative index of activity of the products of the invention in local anaesthesia is at least comparable to that of lidocaine hydrochloride and is in many cases 1.5 to 3 times higher.

The spasmolytic activity in vitro as compared with papaverine shows that, apart from the products of Examples 5, 9 and 10, the indices are up to seven times higher than those of the reference for the products of Examples 2 and 21.

Compared with hexamethonium dibromide, the indices are all nearly 7 to 11 times higher in respect of this reference for the products of Examples 3 and 21.

References known by Applicant are U.S. Pat. No. 2,649,445 and French patent 5012 M.

In U.S. patent $R_1$, m and q cannot have the same meanings as in the present invention.

In the french patent the carbon atom which bears $R_1$ is not tetrasubstituted.

What we claim is:

1. Amino-ether oxide of formula:

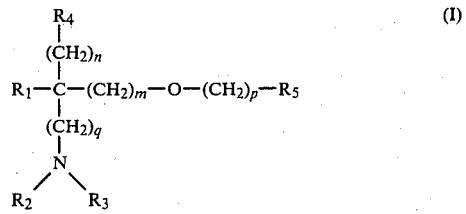

in which:
$R_1$ is lower alkyl,
$R_2$ and $R_3$ which are the same or different are hydrogen or lower alkyl,
$R_4$ is a phenyl or phenoxy nucleus optionally monosubstituted to trisubstituted by substituents which are the same or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, n is equal to zero, 1 or 2, m and q are equal to 0 or 1, p is an integer from 0 to 9 with the proviso that n, m and p are not all equal to 0 when q is equal to 1, and its acid addition salts.

2. Amino-ether oxides according to claim 1, wherein the halogen atoms which appear therein are chlorine atoms or bromine atoms.

3. Amino-ether oxides according to claim 1 or 2, wherein $R_5$ is methyl.

4. Amino-ether oxide according to claim 1, which is 1-[(3,4-dimethoxy)benzyloxymethyl]-1-phenyl-N,N-dimethyl-n-propylamine.

5. Amino-ether oxide according to claim 1, which of 1-[(3,4,5-trimethoxy)benzyloxy]-1-phenyl-N,N-dimethyl-n-propylamine.

6. Amino-ether oxide according to claim 1, which is 1-benzyloxymethyl-1-phenyl-N,N-dimethyl-n-propylamine.

7. Amino-ether oxide according to claim 1, which is 1-[(3,4,5-trimethoxy)benzyloxymethyl]-1-phenyl-N-methyl-n-propylamine.

8. Amino-ether oxide according to claim 1, which is 1-[(4-chloro)benzyloxymethyl]-1-methyl-1-[(4-methoxy)-phenyl]-N,N-dimethylamine.

9. Pharmaceutical agent having antispasmodic, anesthetic and analgesic activities, comprising a physiologically acceptable excipient and an effective amount of an amino-ether oxide of formula:

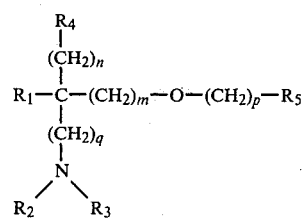

in which:

$R_1$ is lower alkyl, $R_2$ and $R_3$ which are the same or different are hydrogen or lower alkyl, $R_4$ is a phenyl or phenoxy nucleus optionally monosubstituted to trisubstituted by substituents which are the same or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, n is equal to zero, 1 or 2, m and q are equal to 0 or 1, p is an integer from 0 to 9 with the proviso that n, m and p are not all equal to 0 when q is equal to 1 and its pharmaceutically acceptable acid addition salts.

* * * * *

ND REEXAMINATION CERTIFICATE (1193rd)

United States Patent [19]

Torossian et al.

[11] B1 4,301,163
[45] Certificate Issued  Jan. 23, 1990

[54] AMINO-ETHER OXIDES AND USE THEREOF IN THERAPY

[75] Inventors: Diéran R. Torossian, Bourg-la-Reine; Claude P. Roux, Paris; Gilbert G. Aubard, Palaiseau, all of France

[73] Assignee: Societe Industrielle de Produits de Synthese, Aurille, France

Reexamination Request:
No. 90/001,646, Nov. 23, 1988

Reexamination Certificate for:
Patent No.: 4,301,163
Issued: Nov. 17, 1981
Appl. No.: 164,931
Filed: Jul. 1, 1980

[30] Foreign Application Priority Data

Jul. 11, 1979 [FR] France ................................ 7917986

[51] Int. Cl.⁴ .......................................... A61K 31/44
[52] U.S. Cl. ................................... 514/357; 514/646; 546/300; 546/334; 564/346; 564/347
[58] Field of Search ............... 564/346, 347; 514/357, 514/646; 546/292, 300, 334

[56] References Cited

PUBLICATIONS

"Double Addition d'Organometalliques sur des Nitriles α–Oxygenes R'C≡N, Obtention d'Amines Primaires de Type (R'RR')CNH₂", H. Gautier, Journal of Organometallic Chemistry, 140 (1977) 145–155.

*Primary Examiner*—James H. Reamer

[57] ABSTRACT

Amino-ether oxides of formula:

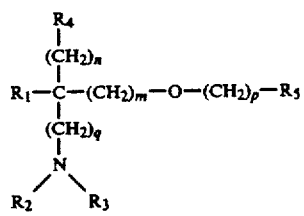

in which $R_1$ is lower alkyl, $R_2$ and $R_3$ which are the same or different are hydrogen or lower alkyl, $R_4$ is a phenyl or phenoxy nucleus optionally monosubstituted to trisubstituted by substituents which are the same or different, halogen or lower alkoxy, $R_5$ is a phenyl radical optionally monosubstituted to trisubstituted by substituents which are the same or different, halogen, lower alkyl, lower alkoxy or nitro, a pyridyl radical or a lower alkyl radical, n is equal to zero, 1 or 2 and p is an integer from 0 to 9, m and q are equal to zero or 1. Local and spasmolytic anaesthetics.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 9 is confirmed.

Claim 3 is cancelled.

Claims 1 and 5 are determined to be patentable as amended.

Claims 2, 4 and 6–8, dependent on an amended claim, are determined to be patentable.

1. Amino-ether oxide of formula:

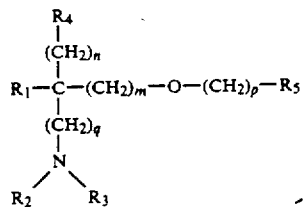

in which;
- $R_1$ is lower alkyl,
- $R_2$ and $R_3$ which are the same or different are hydrogen or lower alkyl,
- $R_4$ is a phenyl or phenoxy nucleus optionally monosubstituted to trisubstituted by substituents which are the same or different, halogen or lower alkoxy,
- $R_5$ is a phenyl radical optionally monosubstituted to trisubstituted by substituents which are the same or different, halogen, lower alkyl, lower alkoxy or nitro, *or a pyridyl radical* [or a lower alkyl radical],
- n is equal to zero, 1 or 2,
- m and q are equal to 0 or 1,
- p is an integer from 0 to 9 with the proviso that n, m and p are not all equal to 0 when q is equal to 1, and its acid addition salts.

5. Amino-ether oxide according to claim 1, which [of] *is* 1-[(3,4,5-trimethoxy)[benzyloxy]*benzyloxymethyl*-1-phenyl-N,N-dimethyl-n-propylamine.

* * * * *